(12) United States Patent
Erkamp et al.

(10) Patent No.: US 12,178,647 B2
(45) Date of Patent: Dec. 31, 2024

(54) SURFACE COMPLIANT ULTRASOUND TRANSDUCER ARRAY

(71) Applicant: KONINKLIJKE PHILIPS N.V., Eindhoven (NL)

(72) Inventors: Ramon Quido Erkamp, Swampscott, MA (US); Shyam Bharat, Arlington, MA (US); Man Nguyen, Melrose, MA (US); Jun Seob Shin, Medford, MA (US); Jean-Luc Francois Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1638 days.

(21) Appl. No.: 16/321,562

(22) PCT Filed: Jul. 21, 2017

(86) PCT No.: PCT/EP2017/068434
§ 371 (c)(1),
(2) Date: Jan. 29, 2019

(87) PCT Pub. No.: WO2018/024501
PCT Pub. Date: Feb. 8, 2018

(65) Prior Publication Data
US 2019/0159761 A1 May 30, 2019

Related U.S. Application Data (60) Provisional application No. 62/370,048, filed on Aug. 2, 2016.

(30) Foreign Application Priority Data

Sep. 12, 2016 (EP) ..................................... 16188235

(51) Int. Cl.
*A61B 8/00* (2006.01)
*A61B 8/06* (2006.01)
(Continued)

(52) U.S. Cl.
CPC .............. *A61B 8/4483* (2013.01); *A61B 8/06* (2013.01); *A61B 8/4254* (2013.01);
(Continued)

(58) Field of Classification Search
CPC ....... A61B 8/4483; A61B 8/4254; A61B 8/06; A61B 8/488; A61B 8/4272;
(Continued)

(56) References Cited

U.S. PATENT DOCUMENTS

| 4,458,689 A | 7/1984 | Sorenson |
| 7,955,266 B2 | 6/2011 | Casula |

(Continued)

FOREIGN PATENT DOCUMENTS

| EP | 1066119 B1 | 11/2004 |
| JP | H01259699 A | 10/1989 |

(Continued)

OTHER PUBLICATIONS

International Search and Written Opinion for International Application No. PCT/EP2017/068434, mailed Oct. 17, 2017, 11 pages.

*Primary Examiner* — Amal Aly Farag (57) ABSTRACT

An ultrasound transducer array includes an array of elongate support members that are displaceable and/or deformable relative to each other in the elongation direction of the elongate support members, each elongate support member having a patient facing surface carrying an ultrasound transducer tile; and multiple sensors, each adapted to detect the
(Continued)

relative displacement and/or deformation of one of the elongate support members. The ultrasound transducer array may be included in an ultrasound system.

20 Claims, 9 Drawing Sheets (51) Int. Cl.
| | |
|---|---|
| A61B 8/08 | (2006.01) |
| A61N 7/00 | (2006.01) |
| A61N 7/02 | (2006.01) |
| B06B 1/02 | (2006.01) |
| B06B 1/06 | (2006.01) |
| G01S 15/89 | (2006.01) |
| G10K 11/00 | (2006.01) |
| A61B 90/00 | (2016.01) |

(52) U.S. Cl.
CPC ............ *A61B 8/4272* (2013.01); *A61B 8/488* (2013.01); *A61N 7/00* (2013.01); *A61N 7/02* (2013.01); *B06B 1/02* (2013.01); *B06B 1/0622* (2013.01); *G01S 15/8925* (2013.01); *G10K 11/004* (2013.01); *A61B 2090/061* (2016.02); *A61B 2562/0204* (2013.01); *A61N 2007/0078* (2013.01); *A61N 2007/0086* (2013.01); *A61N 2007/0091* (2013.01); *B06B 1/0292* (2013.01); *B06B 2201/76* (2013.01)

(58) Field of Classification Search
CPC ...... A61B 2090/061; A61B 2562/0204; A61N 7/00; A61N 7/02; A61N 2007/0091; A61N 2007/0086; A61N 2007/0078; B06B 1/0622; B06B 1/02; B06B 2201/76; B06B 1/0292; G01S 15/8925; G01S 7/52079; G01S 15/8929; G10K 11/004; G10K 11/352

See application file for complete search history.

(56) References Cited

U.S. PATENT DOCUMENTS

| | | | |
|---|---|---|---|
| 2002/0067107 A1* | 6/2002 | Lewis ................. | A61B 8/0825 |
| | | | 310/334 |
| 2005/0146247 A1 | 7/2005 | Fisher et al. | |
| 2005/0225212 A1 | 10/2005 | Scott et al. | |
| 2009/0108710 A1 | 4/2009 | Brown et al. | |
| 2009/0259128 A1 | 10/2009 | Stribling | |
| 2009/0264768 A1* | 10/2009 | Courtney ............ | A61B 5/0086 |
| | | | 600/478 |
| 2010/0262013 A1* | 10/2010 | Smith ................. | A61B 8/4254 |
| | | | 600/459 |
| 2013/0204136 A1* | 8/2013 | Duric ................. | G01S 15/8927 |
| | | | 600/448 |
| 2014/0235962 A1* | 8/2014 | Yu ............................ | A61N 7/00 |
| | | | 600/301 |
| 2015/0208947 A1* | 7/2015 | Tojo ..................... | A61B 5/065 |
| | | | 600/104 |
| 2016/0256133 A1 | 9/2016 | Dekker et al. | |

FOREIGN PATENT DOCUMENTS

| | | |
|---|---|---|
| JP | 2005195495 A | 7/2005 |
| WO | 2016063163 A1 | 4/2016 |

* cited by examiner

SURFACE COMPLIANT ULTRASOUND TRANSDUCER ARRAY

This application is the U.S. National Phase application under 35 U.S.C. § 371 of International Application No. PCT/EP2017/068434, filed on Jul. 21, 2017, which claims the benefit of Provisional Application Ser. No. 62/370,048, filed Aug. 2, 2016 and European Application Serial No. 16188235.2, filed Sep. 12, 2016. These applications are hereby incorporated by reference herein.

FIELD OF THE INVENTION

The present invention relates to an ultrasound transducer array comprising a plurality of ultrasound transducer tiles.

The present invention further relates to an ultrasound system comprising such an ultrasound transducer array.

The present invention further relates to a method of operating such an ultrasound system.

BACKGROUND OF THE INVENTION

Ultrasound waves find several applications in medicine. One such application is ultrasound imaging, wherein ultrasound waves are emitted by an ultrasound device comprising an array of ultrasound transducers into the body of a patient and echoes of the ultrasound waves are collected by the ultrasound transducers or by dedicated ultrasound receivers and processed to generate an ultrasound image, e.g. a 1D, 2D or 3D ultrasound image. Another application is ultrasound therapy such as high intensity focused ultrasound (HIFU) therapy in which ultrasound beams are generated by an ultrasound device comprising ultrasound transducer element tiles and are focused on diseased tissue. The significant energy deposition at the focus creates local temperatures in the range of about 65° C. to 85° C., which destroys the deceased tissue by coagulative necrosis.

Such ultrasound systems typically comprise an ultrasound transducer array, e.g. as part of an ultrasound probe, for delivering ultrasound waves to a subject, e.g. to a patient being imaged or treated. Such an ultrasound transducer array typically comprises a plurality of ultrasound transducers such as piezoelectric transducer elements formed of materials such as lead zirconate titanate (PZT) or polyvinylidene-fluoride (PVDF) and capacitive micro-machined ultrasonic transducer (CMUT) elements in which a membrane including a first electrode over a cavity comprising a second electrode opposite the first electrode and separated therefrom by the cavity is used to generate the ultrasound waves (or receive the ultrasound waves in a receive mode) through application of an appropriate stimulus, e.g. an alternating current, to the first and second electrodes. Increasingly, several of such ultrasound transducer elements are combined on so-called tiles, e.g. chips of a semiconductor substrate in which the ultrasound transducer elements are located, which tiles may have dimensions of several centimetres squared ($cm^2$) in some applications. This allows for the ultrasound transducer arrays to cover larger areas of the subject's body to be imaged or treated. The ultrasound transducer elements of such tiles may be grouped together and operated in unison, such that the tile behaves as a composite ultrasound transducer element comprising multiple facets, i.e. ultrasound transducer cells combining to form the composite ultrasound transducer element, or alternatively may be operated independently.

For such ultrasound transducer arrays, and in particular for large area ultrasound transducer arrays, e.g. ultrasound transducer arrays comprising a plurality of such ultrasound transducer tiles, it is far from trivial to establish a good conformal contact between the transducer elements of the ultrasound probe and the part of the body to be imaged. For smaller ultrasound probes, this is typically achieved by using special gels that improve the contact between the ultrasound transducer array and the body part. However, a drawback of this approach is that usually large amounts of gel have to be used, which may contain air bubbles that interfere with the transmission or reception of the ultrasound signals. Also, such gel applications may no longer be practically feasible for large area ultrasound transducer arrays to solely produce the conformal and acoustic coupling required between the array and body region on which the array is placed, as it becomes practically impossible to effectively apply the gel to the individual transducer elements, e.g. tiles without this process becoming messy due to the use of excess gel. In some cases, it even becomes impossible to achieve the desired conformal contact between the ultrasound transducer array and the surface of the body portion to receive the array, e.g. due to the relatively large curvature of the surface.

To this end, flexible ultrasound transducer arrays have entered the market, which may exhibit improved compliance with a contoured surface, e.g. a curved portion of a patient's body. An example of such an array is disclosed in EP 1 066 119 B1. For such arrays, a reduced amount of coupling gel may be used, typically to improve acoustic coupling as the desired conformal coupling is largely achieved by the flexibility of the transducer array. However, operation of such ultrasound transducer arrays is not without challenges. In such arrays, the ultrasound transducer tiles have several degrees of freedom, e.g. translational freedom in the X, Y, Z-plane as well as tip/tilt freedom. In order to achieve coherent beamforming in such scenarios, the actual orientation (relative positions) of each ultrasound transducer tile must be known to the beamforming circuitry of an ultrasound system deploying such an ultrasound transducer array. This is not straightforward, and typically requires the inclusion of expensive orientation sensors associated with individual tiles.

SUMMARY OF THE INVENTION

The present invention seeks to provide more cost-effective ultrasound transducer arrays for coherent beamforming that can sufficiently conform to three-dimensional surfaces.

The present invention further seeks to provide an ultrasound system comprising such an ultrasound transducer array.

The present invention yet further seeks to provide a method of operating such an ultrasound system.

According to an aspect, there is provided an ultrasound transducer array comprising an array of elongate support members displaceable and/or deformable relative to each other in the elongation direction of said elongate support members, each elongate support member having a patient facing surface carrying an ultrasound transducer tile; and a plurality of sensors, each adapted to detect the relative displacement and/or deformation of one of said elongate support members. In the embodiments of the ultrasound transducer array of the present invention, the elongate support members of the ultrasound transducer array only have a single degree of translational freedom, i.e. in the elongation direction of the elongate support members such that each elongate support member can independently move towards or away from a surface, e.g. a body surface, onto which the ultrasound transducer array is positioned. Such a single degree of freedom may be detected using relatively simple sensors, for example by each elongate support member comprising at least one of said sensors to detect the displacement and/or deformation of the associated elongate support member, e.g. a neighboring or adjacent elongate support member, thereby providing a cost-effective ultrasound transducer array which can comply with contoured surfaces due to the aforementioned degree of translational freedom of the individual elongate support members.

In an embodiment, each sensor is an optical sensor facing a surface along said elongation direction of an adjacent elongate support member, said surface carrying an optical pattern for detecting the relative displacement of said adjacent elongate support member. In this manner, the relative displacement and/or deformation of an elongate support member may be detected in a straightforward manner by evaluation of the optical pattern with the optical sensor.

The optical pattern may comprise a location-unique coding pattern, which has the advantage that an absolute orientation (displacement) of the elongate support member may be determined without requiring a calibration, for example by deployment of an absolute position optical sensor.

The ultrasound transducer array may further comprise a locking mechanism for locking the respective displacement and/or deformation of the elongate support members. This ensures that the respective relative displacements and/or deformations of the elongate support members is fixed or frozen during use of the ultrasound transducer array, thereby avoiding the risk of inadvertent displacements of one or more elongate support members during use disrupting the operation (or operational accuracy) of the ultrasound transducer array. For example, said locking mechanism may comprise an adjustable strap surrounding the ultrasound transducer array, which by tightening the strap may cause increased friction between neighboring elongate support members, thereby increasing the force required to displace or deform individual elongate support members and therefore reducing the risk of such inadvertent displacements.

The elongate support members may have a polygonal cross-section normal to said elongation direction. This may be a square or otherwise rectangular polygonal cross-section although embodiments of the present invention are not limited thereto; triangular, hexagonal, octagonal cross-sections and so on are equally feasible.

In an embodiment, at least one of the elongate support members is removable from the ultrasound transducer array. This has the advantage that a removable elongate support member may be replaced by a medical instrument (including, but not limited to, needles, cannulas, dilators, catheters and guidewires), for example to facilitate ultrasound guided interventional procedures.

In another embodiment, the patient facing surfaces define a contoured surface. Such a contoured surface may roughly match the contours of a surface portion, e.g. a contoured body surface portion, to be contacted by the ultrasound transducer array, such that each elongate support member requires relatively small displacements and/or deformations along its elongation direction in order to achieve the desired conformal contact with the contoured surface. This for example is advantageous in terms of ultrasound beamforming, where the diverging nature of an ultrasound beam portion formed by a single ultrasound transducer tile may interfere with a side wall of an adjacent elongate support member in case of a large displacement of the adjacent elongate support member relative to the elongate support member carrying the ultrasound transducer tile. Hence, such a contoured surface may assist in avoiding or at least reducing the occurrence of artefacts in ultrasound beams formed with the ultrasound transducer array that are the result of such interference.

For example, each patient facing surface may comprise a conformable coupling layer to assist the formation of such a contoured surface with the patient facing surfaces of the ultrasound transducer array.

In an embodiment, each ultrasound transducer tile comprises an array of ultrasound transducer elements. This for example facilitates the formation of large area ultrasound transducer arrays, e.g. arrays capable of covering several hundreds or thousands of centimetres squared ($cm^2$) of a surface such as a body surface to be contacted by the ultrasound transducer array.

According to another aspect, there is provided an ultrasound system comprising a control unit and the ultrasound transducer array of any of embodiments described in the present application, wherein the control unit is arranged to operate the ultrasound transducer tiles in response to sensor data provided by the plurality of sensors. Such an ultrasound system benefits from the limited degrees of freedom, i.e. a single translational degree of freedom in the elongation direction of the elongate support members, of the ultrasound transducer array in that the complexity of the control unit may be reduced, thereby potentially reducing the cost of the ultrasound system beyond the cost savings provided by the ultrasound transducer arrays according to embodiments of the present invention.

According to yet another aspect, there is provided a method of operating such an ultrasound system, the method comprising positioning the ultrasound transducer array on a surface; receiving sensor data from the plurality of sensors indicative of the respective relative displacements and/or deformations of the elongate support members caused by said positioning; and determining the respective relative displacements and/or deformations of the elongate support members from the received sensor data. This provides a straightforward operating method of such an ultrasound system, which may be implemented in a cost-effective manner as explained in more detail above.

The method may further comprise fixating the relative positions of the elongate support members upon positioning the ultrasound transducer array on said surface to avoid accidental displacement of one or more elongate support members during use of the ultrasound transducer array as explained in more detail above.

The method may further comprise excluding at least part of an ultrasound transducer tile on an elongate support member having a displacement and/or deformation relative to a neighboring elongate support member exceeding a defined threshold in order to avoid beamforming artefacts caused by partial blockage of a diverging beam portion by an adjacent elongate support member as explained in more detail above.

In an embodiment, the method futher comprises operating the ultrasound transducer array in accordance with the determined respective relative displacements and/or deformations of the elongate support members.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
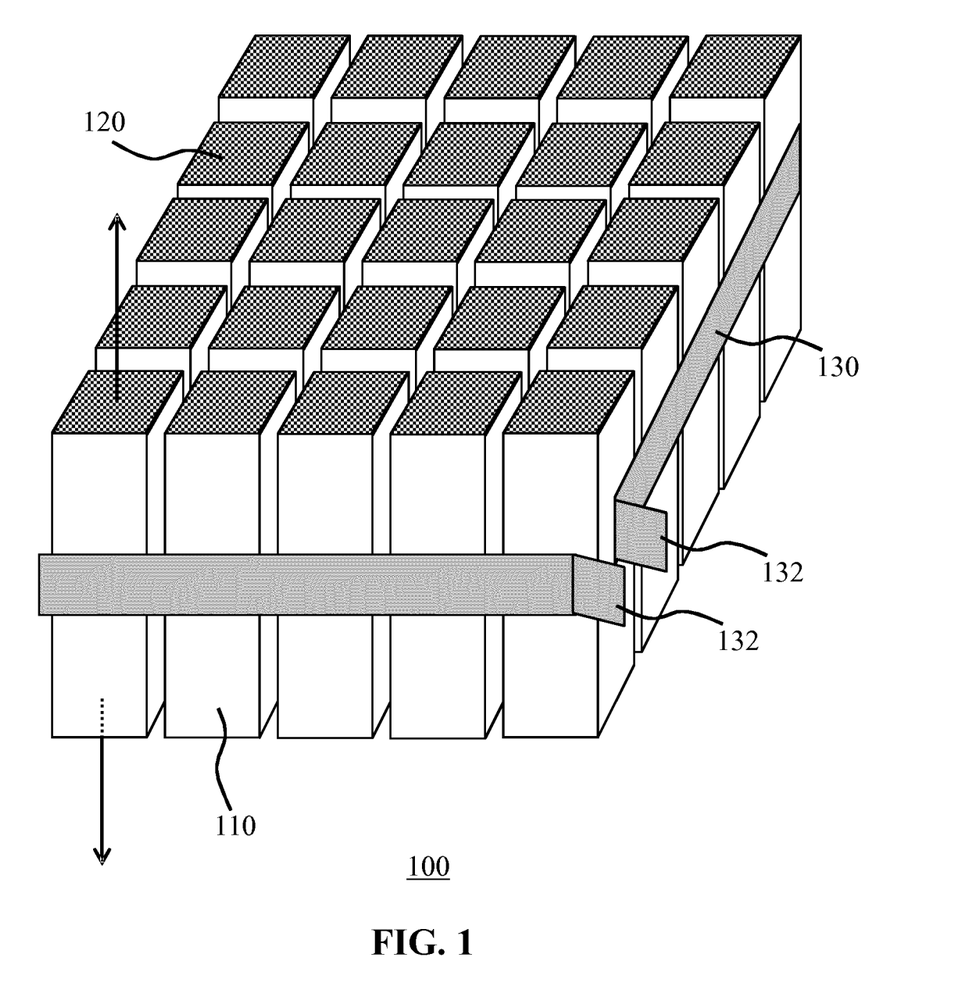
FIG. 1 schematically depicts an ultrasound transducer array according to an embodiment.

FIG. 1 schematically depicts an ultrasound transducer array 100 according to an example embodiment. The ultrasound transducer array 100 comprises a plurality of elongate support members 110, e.g. support bars, arranged in a M×N grid, in which M and N each are positive integers, for example of a value of at least 5, 8, 10, 12, 15, 20, and so on. Other values are equally feasible. M and N may be the same, in which case the grid may be a square grid, or M and N may be different, in which case the grid may be an oblong grid. Other grid shapes equally may be contemplated. Each elongate support members 110 typically has a single degree of translational freedom in its elongation direction as indicated by the arrows extending from the elongate support member 110 in the bottom left corner of the ultrasound transducer array 100. This allows each elongate support member 110 to be pushed towards or away from a surface, e.g. a contoured surface such as a contoured body portion, onto which the ultrasound transducer array 100 is positioned, thereby allowing each elongate support member 110 to contact a contoured surface 150 as schematically depicted in the cross-sectional view of FIG. 2., where the elongate support members 110 have been displaced in their elongation direction, i.e. the Z-direction in the Cartesian coordinate frame shown in FIG. 2. Alternatively or additionally, the elongate support members 110 may be deformable, e.g. compressible, in this direction only. In the remainder of this description, where reference is made to displacement, this is intended to also cover displacement by such deformation.

Figure 2:
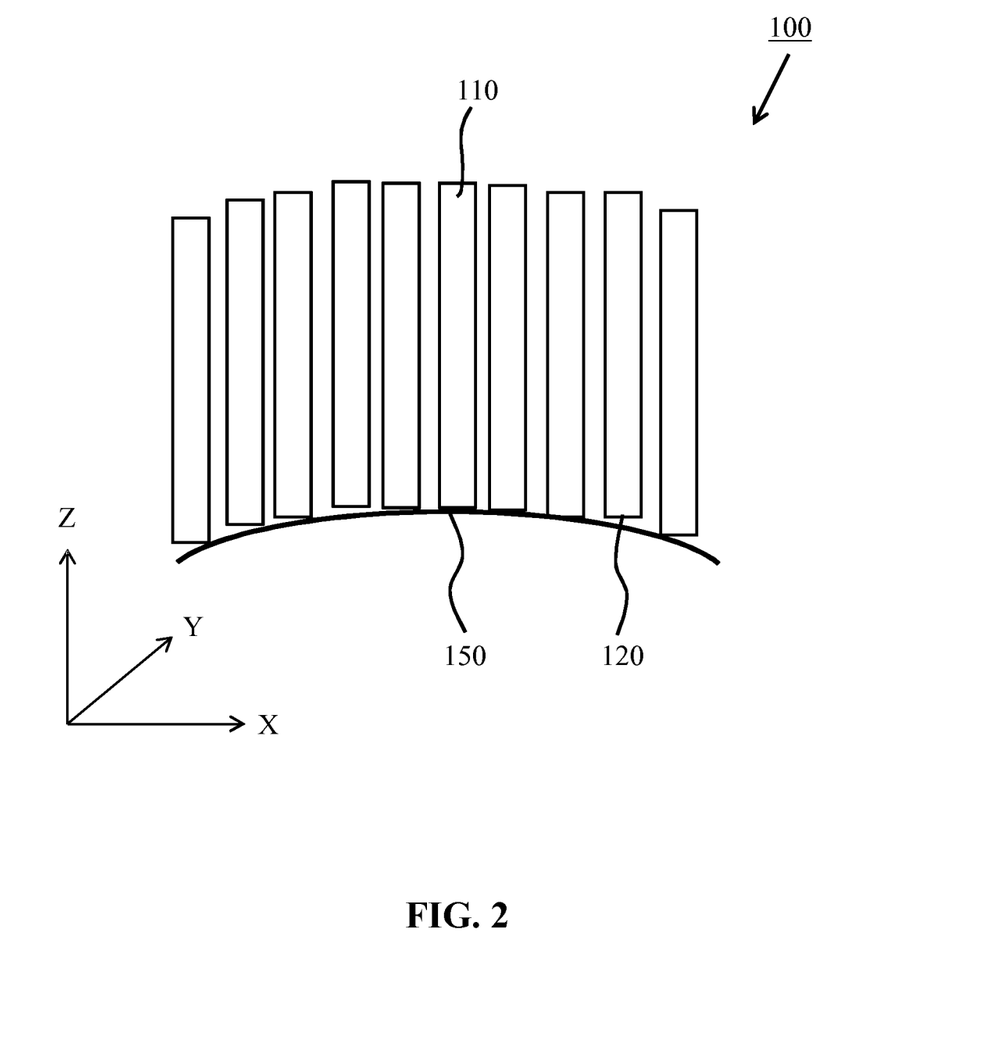
FIG. 2 schematically depicts an ultrasound transducer array according to an embodiment in use.

The elongate support members 110 each further comprise a patient facing surface normal to their elongation direction, i.e. a surface facing the surface 150 to be contacted by the ultrasound transducer array 100, with each patient facing surface carrying an ultrasound transducer tile 120. Such an ultrasound transducer tile 120 may comprise one or more ultrasound transducer elements. For example, the ultrasound transducer elements may be implemented by a piezoelectric ceramic material such as a lead zirconate titanate (PZT)-based material, a piezoelectric single crystal or composite material, a capacitive micromachined ultrasound transducer (CMUT) and so on.

The ultrasound transducer element tiles 120 may have any suitable shape, e.g. a circular shape or polygonal shape. The shape of the ultrasound transducer element tile 120 preferably matches the cross-sectional shape of the elongate support member 110 at which the ultrasound transducer tile 120 is mounted, i.e. a cross-sectional shape normal to the elongation direction of the elongate support member 110, that is, the cross-sectional shape of the elongate support member 110 in the X-Y plane as shown in FIG. 2. A polygonal shape such as a rectangular, e.g. square, shape is particularly mentioned as such a shape facilitates a close packing of the ultrasound transducer element tiles 120 within the transducer array, wherein the gap between adjacent ultrasound transducer element tiles 120 is minimized. The avoidance of relatively large gaps between adjacent ultrasound transducer element tiles 120 ensures that a substantially continuous image may be generated with the ultrasound transducer array 100 and may at least reduce the formation of ultrasound artefacts such as grating lobes. Other suitable polygonal cross-sections include triangular, hexagonal and octagonal cross-sections for instance. Each ultrasound transducer tile 120 may have a transducer surface area of several mm$^2$ to several cm$^2$ e.g. 0.1-100 cm$^2$, to form a large area ultrasound transducer array 100. It should be understood that other area dimensions may be contemplated; for example, the ultrasound transducer array 100 is not necessarily a large area ultrasound transducer array 100.

The ultrasound transducer array 100 may be for transmitting ultrasonic waves, e.g. ultrasound pulses, and receiving (pulse) echo information in case the ultrasound transducer array 100 forms part of an ultrasound diagnostic imaging system. Alternatively, the ultrasound transducer array 100 may be adapted to generate focused ultrasound waves in case the ultrasound transducer array 100 forms part of an ultrasound therapy system such as a HIFU therapy system.

The elongate support members 110 may be made of any suitable material or combination of materials. The elongate support members 110 preferably are rigid bodies to suppress deformation of the elongate support members 110 in a direction other than the elongation direction of the elongate support members 110, as such deformations may lead to undesirable translation, tipping and/or tilting of the ultrasound transducer tiles 120 on the elongate support members. For example, the elongate support members 110 may be made of a rigid backing material such as a resin in which ultrasound scattering and/or absorbing bodies are dispersed. For instance, the ultrasound scattering bodies may be hollow glass beads or other suitable body that can be used for ultrasound scattering. The ultrasound absorbing bodies may be bodies made of one or more heavy elements. For instance, the ultrasound absorbing bodies may be particles comprising tungsten, such as tungsten oxide particles. Such backing materials are well-known per se and are therefore not explained in further detail for the sake of brevity only. It suffices to say that any suitable backing material may be used to form the elongate support members 110. It is furthermore noted that the material(s) used to form the elongate support members 110 is not limited to such backing materials; any suitable material or combination of materials may be used to form the elongate support members 110. For example, each elongate support member 110 may comprise a slice of backing material on a further carrier, e.g. a metal, metal alloy, polymer, ceramic carrier and so on, in which the slice of backing material separates the carrier from the ultrasound transducer tile 120. Other suitable arrangements will be apparent to the skilled person. In an embodiment, at least some of the elongate support members 110 of the ultrasound transducer array 100 may be removable from the array, for example such that the elongate support member may be replaced by a medical instrument dimensioned to fit into the space left behind by the removed elongate support member(s) 110, e.g. for performing a guided interventional (in-vivo) procedure such as an endoscopy supported by ultrasound imaging, an ablation or angioplasty procedure, a biopsy, and so on.

The ultrasound transducer array 100 may further comprise a locking mechanism 130 such as a locking clamp or strap surrounding the grid of elongate support members 110 as schematically depicted in FIG. 1. Such a locking mechanism 130 is arranged to prevent or hinder the respective displacement of the elongate support members 110 upon engagement of the locking mechanism 130 such that the relative displacement of the respective elongate support members 110 after positioning of the ultrasound transducer array 100 on the surface 150 may be locked or frozen. In this manner, the risk of accidental displacement of one or more elongate support members 110 during use of the ultrasound transducer array 100 may be significantly reduced. It will be understood that such accidental displacement is highly undesirable, as changes in the relative displacement of the elongate support members 110 respective to each other may alter the required timing and shape of the ultrasound beam portions to be formed by the ultrasound transducer tiles 120 carried by the (displaced) elongate support members 110 in order to ensure coherent beam forming with the ultrasound transducer array 100.

In an embodiment, the locking mechanism 130 may be user-activated. For example, the locking mechanism 130 may be engaged using a nut and bolt or the like, with the bolt extending through opposite ends 132 of a locking clamp or strap such that tightening of the nut may force the opposing ends 132 together, thereby decreasing the cross-section of the locking clamp or strap and forcing the individual elongate support members 110 together to increase friction between adjacent elongate support members 110. Other suitable locking mechanisms will be immediately apparent to the skilled person, e.g. electromagnetic, pneumatic or hydraulic locking mechanisms, and so on. The locking mechanism 130 may be manually activated or may be activated by an actuator under control of a user interface device such as a foot pedal, a push button on the ultrasound transducer array 100, a voice command interpreted by a speech recognition system, and so on. Many other examples of suitable user interface devices will be immediately apparent to the skilled person.

Figure 3:
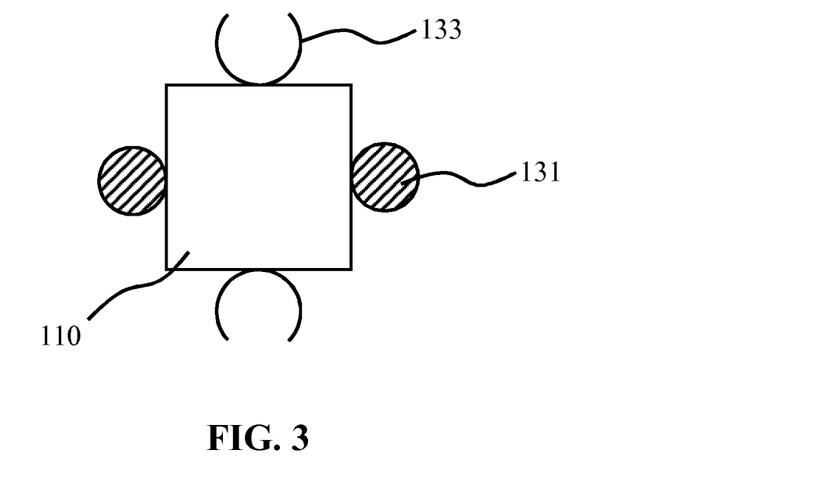
FIG. 3 schematically depicts an aspect of an ultrasound transducer array according to another embodiment.
Figure 4:
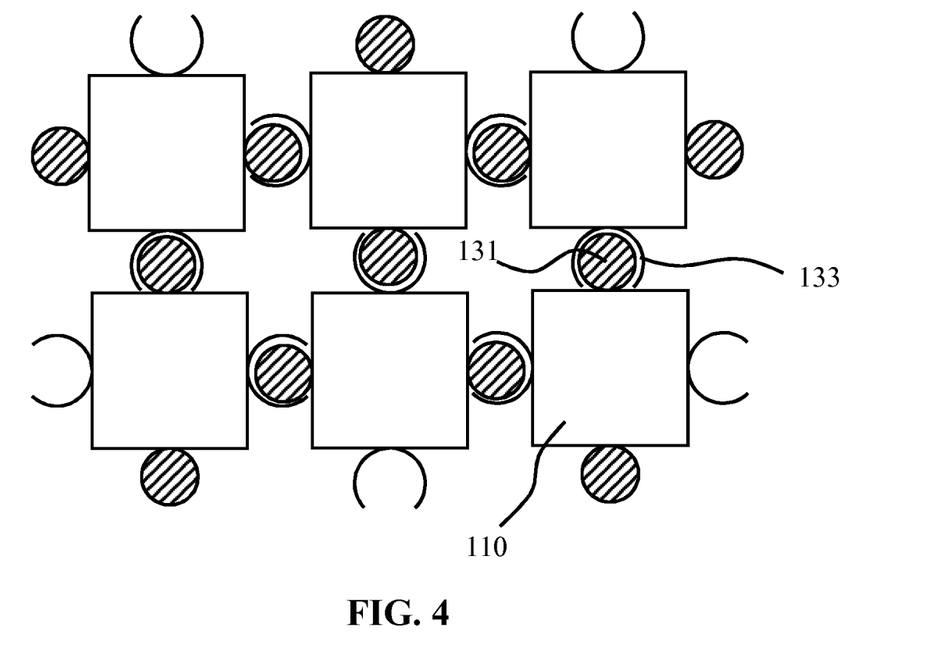
FIG. 4 schematically depicts another aspect of an ultrasound transducer array according to another embodiment.

FIG. 3 schematically depicts a top view of an elongate support member 110 of an ultrasound transducer array 100 according to another embodiment. In this embodiment, the locking mechanism 130 is implemented as a friction arrangement in which each elongate support member 110 comprises an arrangement of guide members 131 and/or guide channels 133 for receiving a guide member 131 extending along respective elongate side surfaces of the elongate support member 110 in its elongation direction. As can be seen in FIG. 4, each guide channel 133 may receive a guide member 131 such that the ultrasound transducer array 100 may be formed in a jigsaw puzzle-style assembly. The guide members 131 and guide channels 133 are dimensioned such that a guide member 131 snugly fits into an opposing guide channel 133 on an adjacent elongate support member 110. Consequently, the friction between the guide member 131 and the guide channel 133 into which the guide member 131 is fitted retains the relative orientation between the respective elongate support members 110 associated with the guide member 131 and the guide channel 133, i.e. adjacent elongate support members 110, unless a sufficiently large force in the elongation direction (Z-direction) of the elongate support members 110 is applied, e.g. by a user pressing the ultrasound transducer array 100 against a contoured surface 150. The guide members 131 and the guide channels 133 may be made of any suitable material and preferably form an integral part of the elongate support members 110. For example, the elongate support members 110 may be made using a suitable moulding or casting technique in which the elongate support members including the guide members and guide channels are formed.

Figure 5:
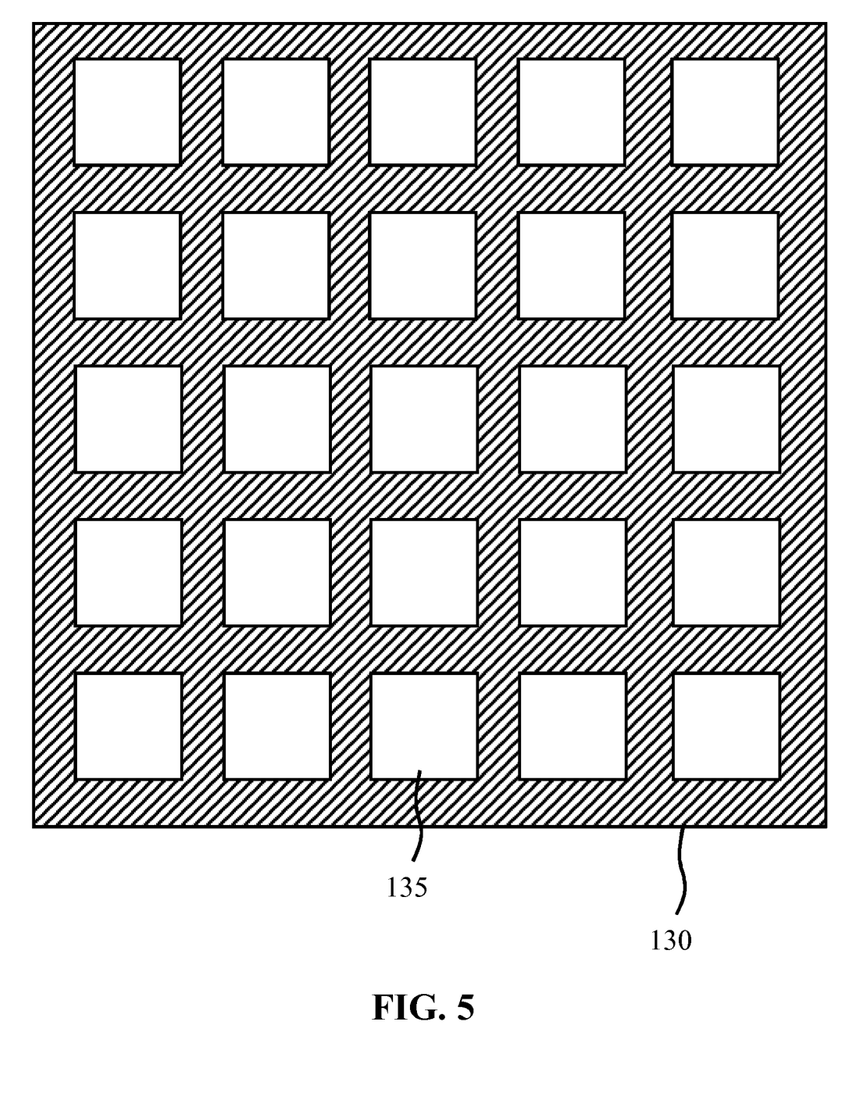
FIG. 5 schematically depicts an aspect of an ultrasound transducer array according to yet another embodiment.

An alternative embodiment of such a friction fitting arrangement is schematically depicted in FIG. 5, in which the ultrasound transducer array 100 may contain a locking mechanism 130 in the form of a mounting frame comprising apertures 135 for receiving the respective elongate support members 110. As will be understood from the foregoing, each aperture 135 is dimensioned such that a corresponding elongate support member 110 snugly fits into the aperture, thereby retaining the relative position of the elongate support member 110 unless a sufficiently large force is applied to the elongate support member 110 in its elongation direction as previously explained. Such a mounting frame may be made of any suitable material. For example, the mounting frame may be made of a polymer material using a moulding or casting technique, may be made of a metal or metal alloy in which the apertures 135 are stamped or otherwise formed in a metal or metal alloy sheet, and so on.

Figure 6:
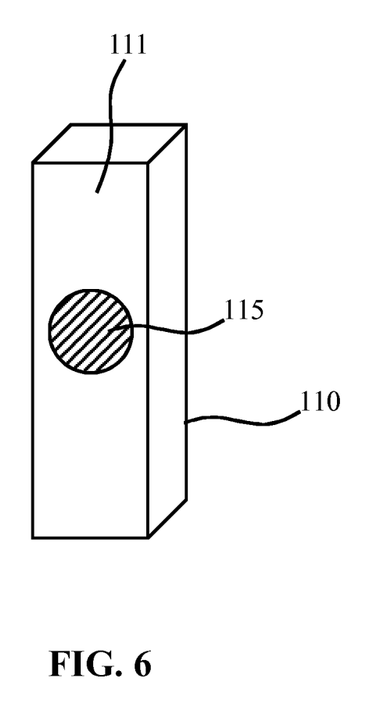
FIG. 6 schematically depicts a first aspect of an ultrasound transducer array according to an embodiment.

The ultrasound transducer array 100 further comprises a plurality of sensors to detect the relative displacement of one of the elongate support members 110, e.g. the displacement of an elongate support member 110 relative to an adjacent elongate support member within the ultrasound transducer array 100. Any suitable arrangement of such sensors may be provided. For example, as schematically depicted in FIG. 6, each elongate support member 110 may comprise at least one optical sensor 115 mounted in or on an elongate side surface 111 of the elongate support member 110. Any suitable optical sensor may be used for this purpose, such as for example a charge coupled device (CCD) or optical sensors used in optical user interfaces such as a computer mouse, which are particularly cost-effective embodiments of such optical sensors.

Figure 7:
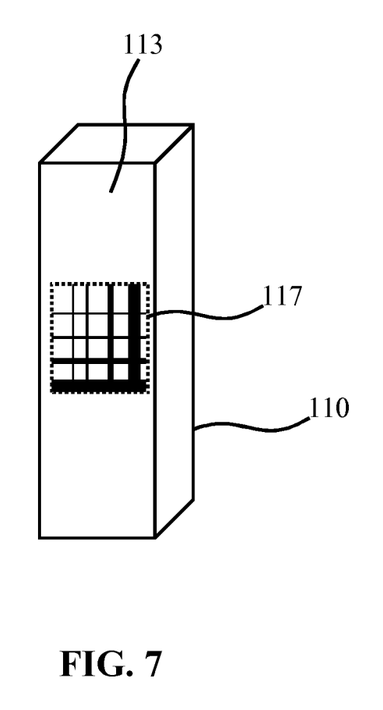
FIG. 7 schematically depicts a second aspect of an ultrasound transducer array according to an embodiment.

The optical sensor 115 may be facing a further elongate side surface 113 of an adjacent (neighboring) elongate support member 110 carrying an optical pattern 117 as schematically depicted in FIG. 7. Such an optical pattern 117 may be formed as a location-unique pattern, i.e. a pattern that varies as a function of a displacement of the elongate support member 110 carrying the pattern in in its elongation direction (or of a displacement of the elongate support member 110 including the optical sensor 115 facing the optical pattern 117) such that the displacement of these elongate support members 110 relative to each other may be determined from the part of the optical pattern 117 detected by the optical sensor 115 facing the optical pattern.

By way of non-limiting example, the optical pattern 117 may comprise a set of horizontal and vertical lines that for instance vary in thickness, colour, and so on in the elongation direction of the elongate support member 110 carrying the optical pattern 117 such that for each displacement of the elongate support member 110 the optical pattern 117 provides a unique fingerprint from which the relative displacement may be determined. By collecting the sensor data provided by the optical sensors 115 across the entire ultrasound transducer array 100, the relative displacements of each elongate support member 110 in the ultrasound transducer array 100 may be mapped. This mapping information may be used by an ultrasound system coupled to the ultrasound transducer array, e.g. by beamforming circuitry of the ultrasound system, in order to control the respective ultrasound transducer tiles 120 on the elongate support members 110 such that a coherent ultrasound beam may be formed with the ultrasound transducer array 100, e.g. by delaying the generation of ultrasound beam portions by a first ultrasound transducer tile 120 relative to a further ultrasound transducer tile 120 as a function of the displacement of the first ultrasound transducer tile 120 relative to the further ultrasound transducer tile 120 or by factoring in this relative displacement in processing received ultrasound pulse echoes with the ultrasound transducer array 100 in case of the ultrasound transducer array 100 forming part of an ultrasound imaging system.

The ultrasound transducer array 100 may comprise K−1 position sensors 115, e.g. optical sensors, in case of an array comprising K elongate support members 110, wherein K is a positive integer; e.g. K=M×N. This ensures that the relative position of each elongate support member 110 may be determined. However, it should be understood that the ultrasound transducer array 100 may comprise additional position sensors, for example to perform error-checking. In an embodiment, the relative displacement of each elongate support member 110 may be determined by at least two position sensors 115 in order to improve the accuracy of the relative displacement determination.

In an embodiment, the elongate support members 110 may move freely, i.e. having the same resistance along the entire displacement, in the elongation direction. However, in an alternative embodiment, each elongate support member 110 may be arranged to be displaced in a stepwise fashion, e.g. by the provision of a plurality of notches or the like on the elongate support members 110 and/or on a mounting frame of the elongate support members 110 such that the respective elongate support members 110 may be displaced in discrete steps along their elongation direction. The steps taken by respective elongate support members 110 may be registered, e.g. using suitable sensors, in order to determine the displacement of the respective elongate support members 110 along their elongation direction. This has the advantage that a sensor arrangement, e.g. an optical sensor arrangement, with a limited resolution may be used, which may be more cost-effective.

Figure 8:
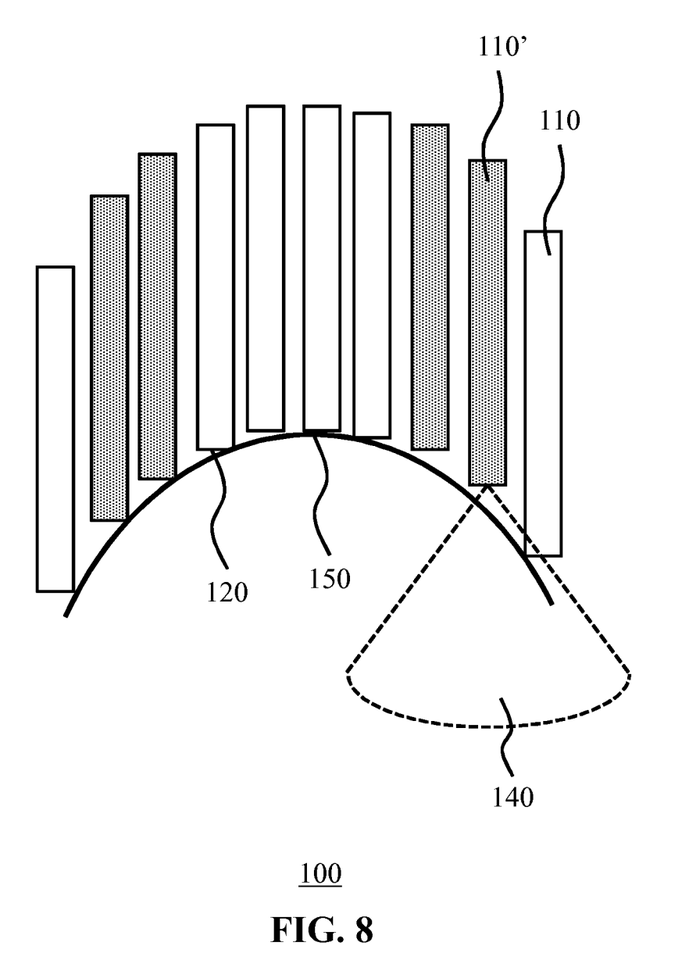
FIG. 8 schematically depicts an ultrasound transducer array according to a further embodiment in use.

The ultrasound transducer array 100 according to embodiments of the present invention has the ability to conform to a highly contoured surface 150, as schematically depicted in the cross-sectional view of FIG. 8. However, a potential problem that may arise when placing the ultrasound transducer array 100 on such highly contoured surfaces, e.g. a highly contoured body portion, is that the displacement of an elongate support member 110 relative to its adjacent relative support members 110' may be relatively large such that part of the body of the elongate support member 110 may partially block the acoustic aperture 140, i.e. the ultrasound beam portion, of the ultrasound transducer tiles 120 on adjacent elongate support members 110'. Such interference may significantly deteriorate the coherence of the ultrasound beam generated with the ultrasound transducer array 100 as the interference may cause unwanted reflections of ultrasound waves, e.g. reverberation artefacts, which reflections may interfere with ultrasound waves generated by other ultrasound transducer tiles 120 in the ultrasound transducer array.

In order to avoid or at least reduce the occurrence of such interference, in a mode of operation of the ultrasound transducer array 100, it may be checked if such interference is likely to occur by comparing the displacement of an elongate support member 110 relative to its neighboring elongate support members 110' as derived from the sensor signals provided by the plurality of sensors in the ultrasound transducer array 100 and then disabling selected ultrasound transducer tiles 120 associated with these elongate support members if the displacement exceeds a defined threshold indicative of the elongate support member 110 entering the acoustic field 140 of the ultrasound transducer tile 120 on a neighboring elongate support member 110'. This is schematically depicted in FIG. 8 by the shaded elongate support members 110'. The ultrasound transducer tiles 120 mounted on the shaded elongate support members 110' are not used in the ultrasound beam forming (or ultrasound pulse echo reception) to avoid the occurrence of such interference artefacts. For example, such ultrasound transducer tiles 120 may be deselected by the beamforming circuitry of the ultrasound system utilizing the ultrasound transducer array 100 based on the relative displacement information received from the plurality of sensors in the ultrasound transducer array 100. Alternatively, only certain elements in a multi-element transducer tile may be deselected, based on the relative displacement information. For example, a few elements on the right side of element 110' may be deselected when forming a beam steering to the right side of the acoustic field 140.

Figure 9:
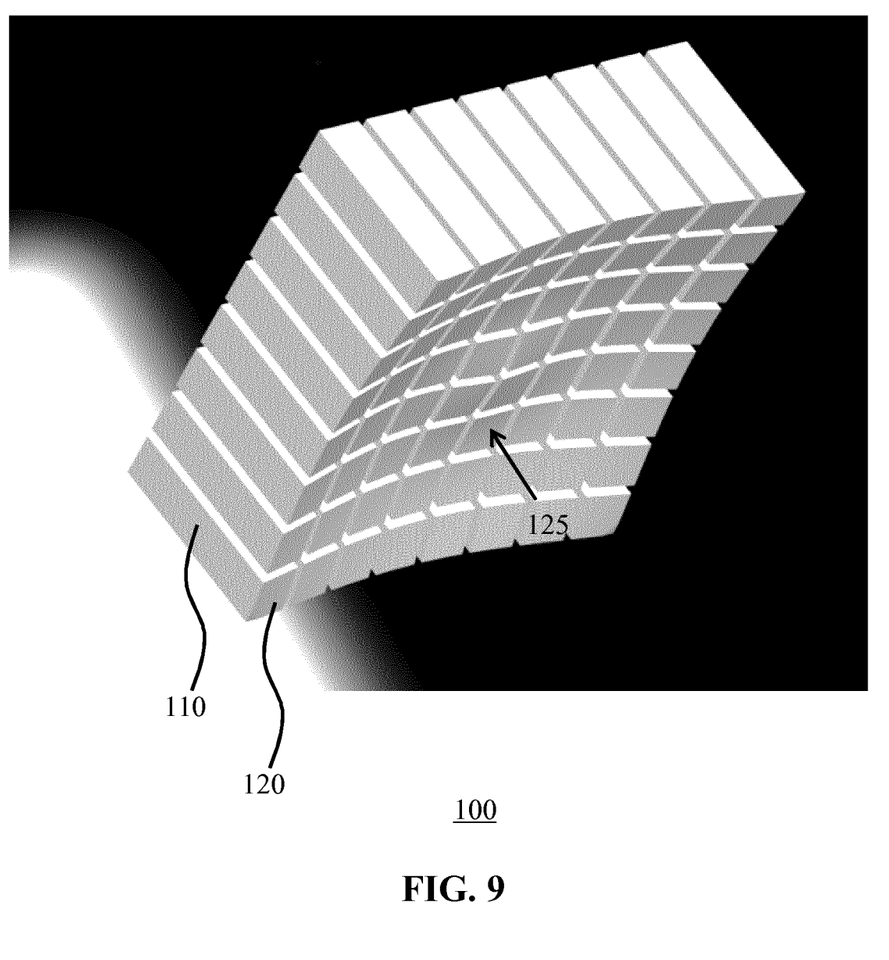
FIG. 9 schematically depicts an ultrasound transducer array according to yet another embodiment.

In order to further reduce the risk of such interference artefacts occurring, the respective patient facing surfaces of the elongate support members 110 on which the respective ultrasound transducer tiles 120 are mounted may be shaped such that the respective patient facing surfaces combined to form a contoured surface 125 as schematically depicted in FIG. 9. Such a contoured surface 125 for instance may be designed to match a commonly occurring shape of a surface 150, e.g. a body surface, onto which the ultrasound transducer array 100 is to be positioned. Consequently, the required displacement for each elongate support member 110 to achieve the desired conformal contact between the ultrasound transducer array 100 and the receiving surface 150 will be significantly reduced compared to an ultrasound transducer array 100 comprising a planar patient facing surface 125, thereby reducing the risk of interference artefacts occurring due to relatively large displacements of at least some of the elongate support members 110 in order to achieve such conformal contact. This therefore has the advantage that a larger number of ultrasound transducer tiles 120 in the ultrasound transducer array 100 may be available for use, which may improve the quality of the ultrasound beam formed with the ultrasound transducer array 100 and/or the image quality of an image of formed by an ultrasound imaging system employing the ultrasound transducer array 100.

In this embodiment, the respective ultrasound transducer tiles 120 may be mounted under a non-perpendicular angle with the elongation direction of the elongate support member 110 onto which the ultrasound transducer tiles 120 are mounted. However, because this non-perpendicular angle is fixed (i.e. the only degree of freedom for each elongate support member 110 is the translational degree of freedom along the elongation direction), configuration of the ultrasound transducer array 100 is equally straightforward because the respective orientations of the ultrasound transducer tiles 120 only need to be specified once, e.g. may be hard-coded into the ultrasound system deploying the ultrasound transducer array 100.

Alternatively or additionally, the patient facing surface 125 may carry a conformal coupling layer (not shown) to reduce the required displacements in the Z-direction to achieve the desired conformal coupling between the ultrasound transducer array 100 and the surface 150. Such a conformal coupling layer may be a pliable or flexible layer further functioning as the acoustic window of the ultrasound transducer tiles 120, e.g. to provide impedance matching between the ultrasound transducer tiles 120 and the surface 150. Such impedance matching materials are well-known per se and it should be understood that any suitable impedance matching material may be used for this purpose.

Figure 10:
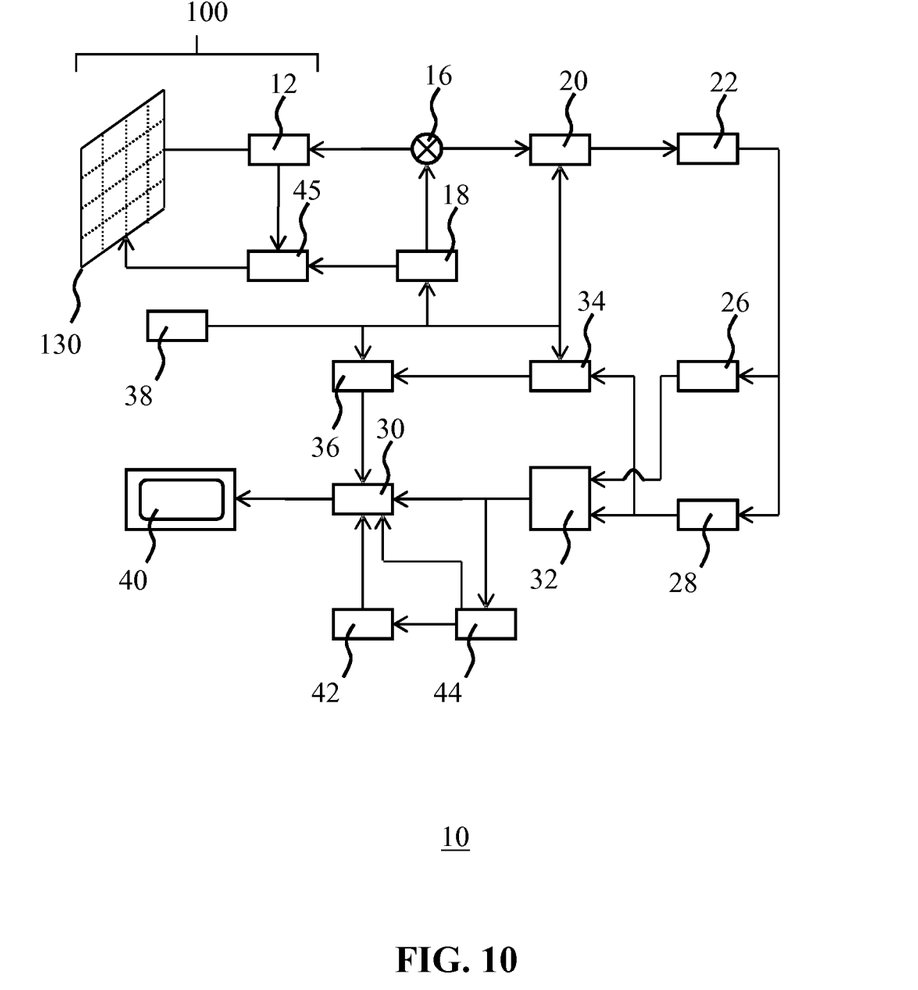
FIG. 10 schematically depicts a circuit diagram of an ultrasound system according to an example embodiment.

The ultrasound transducer array 100 according to embodiments of the present invention may form part of an ultrasound system 10. The ultrasound system 10 according to embodiments of the present invention may further comprise electronic circuitry for controlling the ultrasound probe 100 and for processing the ultrasound (pulse) echoes collected by the ultrasound probe 100 in case of an ultrasound diagnostic imaging system. Such electronic circuitry may at least partially be housed in a control unit such as a user console or the like as is well-known per se. FIG. 10 shows an example embodiment of the electronics that may be deployed to interface with and control the ultrasound transducer array 100 for the generation of ultrasound waves, e.g. ultrasound pulses, and reception of ultrasound echoes, e.g. pulse echoes, e.g. for diagnostic imaging purposes. The transducer array may be coupled to a microbeam former 12 in the ultrasound transducer array 100 which controls transmission and reception of signals by the ultrasound transducer tiles 120. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.)

The microbeam former 12 may be coupled by a probe cable, e.g. coaxial wire, to a terminal or control unit, e.g. a user console device or the like, comprising a transmit/receive (T/R) switch 16 which switches between transmission and reception modes and protects the main beam former 20 from high energy transmit signals when a microbeam former is not present or used and the transducer array is operated directly by the main system beam former 20. The transmission of ultrasonic beams from the transducer array under control of the microbeam former 12 may be directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array, or at different angles for a wider field of view. The transducer controller 18 may be coupled to control a voltage source 45 for the ultrasound transducer array 100. For instance, the voltage source 45 may set the DC and AC bias voltage(s) that are applied to CMUT elements of a CMUT array, e.g. to operate the CMUT elements in collapse mode, as is well-known per se. The transducer controller 18 may be further adapted to control the voltage supply 45 such as to switch the ultrasound transducer element tiles 120 to a low-power mode, e.g. in response to a temperature sensor signal originating from the ultrasound transducer array 100 indicative of the ultrasound transducer element tiles 130 reaching a critical temperature.

The partially beam-formed signals produced by the microbeam former 12 may be forwarded to the main beam former 20 where partially beam-formed signals from individual patches of transducer elements, e.g. transducer tiles, are combined into a fully beam-formed signal. For example, the main beam former 20 may have 128 channels, each of which receives a partially beam-formed signal from a patch of dozens or hundreds of ultrasound transducer cells, e.g. the cells of ultrasound transducer tiles 120. In this way the signals received by thousands of transducer elements of an ultrasound transducer array 100 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the ultrasound transducer array 100 and hence the images produced by the ultrasound transducer array 100 and the ultrasound system 10. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system 10 is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 100 may not have 3D imaging capabilities and so on. Other variations will be apparent to the skilled person.

Moreover, it will be understood that the present invention is not limited to an ultrasonic diagnostic imaging system 10. The teachings of the present invention are equally applicable to ultrasonic therapeutic systems, e.g. HIFU ultrasound systems, in which the ultrasound transducer tiles 120 of the ultrasound transducer array 100 may be operable in transmission mode only as there is no need to receive pulse echoes. As will be immediately apparent to the skilled person, in such therapeutic systems the system components described with the aid of FIG. 10 and required to receive, process and display pulse echoes may be omitted without departing from the teachings of the present application.

Figure 11:
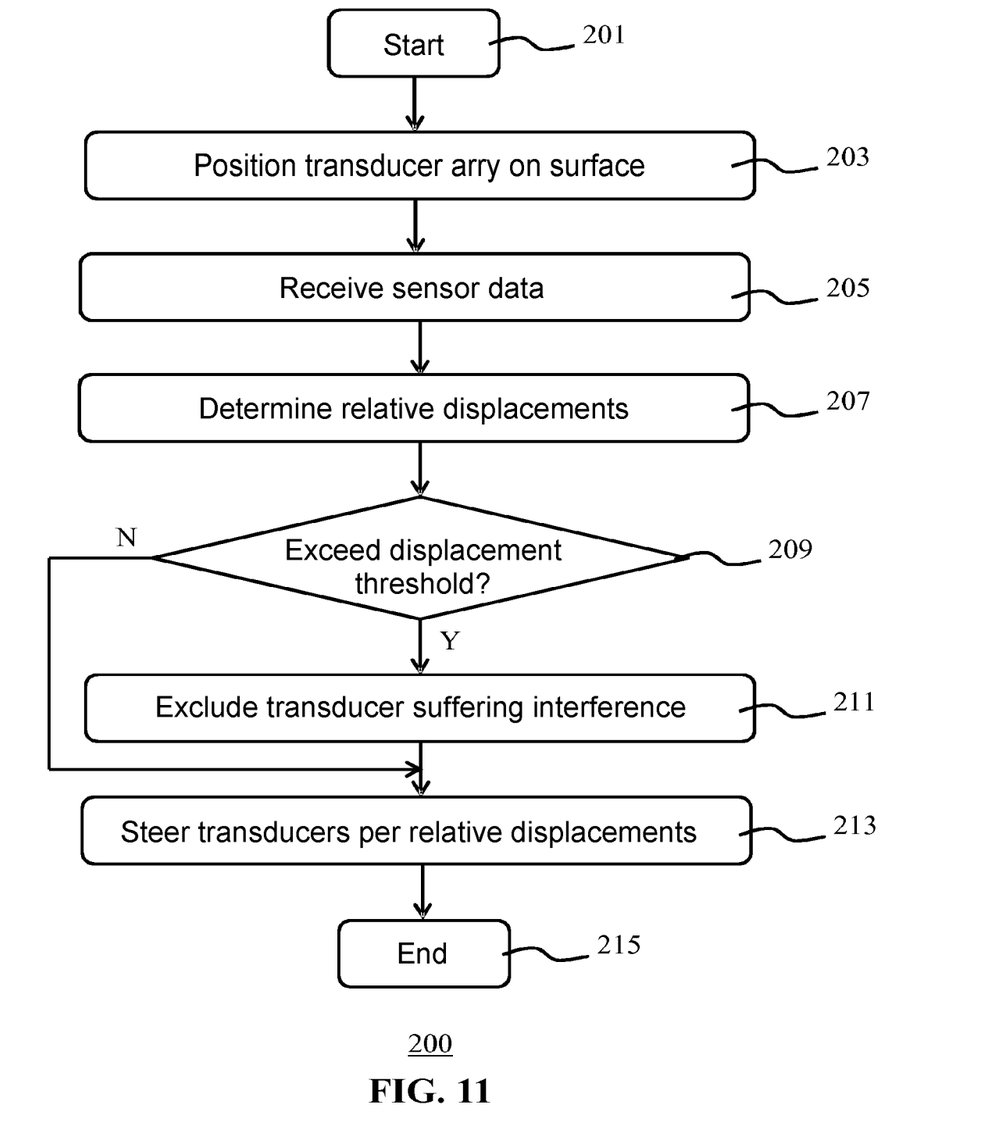
FIG. 11 is a flowchart of an operating method of such an ultrasound system according to an example embodiment.

FIG. 11 is a flowchart of a method 200 for operating an ultrasound system 10 comprising an ultrasound transducer array 100 according to embodiments of the present invention. The method 200 starts in 201, e.g. by the provision of such an ultrasound system 10 including the ultrasound transducer array 100, after which the method 200 proceeds to 203 in which the ultrasound transducer array 100 is positioned on a surface 150, e.g. a body surface, to be subjected to the ultrasound waves generated with the ultrasound transducer array 100 under control of the control unit of the ultrasound system 10. This positioning typically includes the displacement of respective elongated support members 110 in their elongation direction in order to establish the desired conformal contact between the patient facing surface 125 of the ultrasound transducer array 100 and the surface 150. In an embodiment, this positioning may be concluded by fixating (locking) the relative positions of the elongate support members 110 upon positioning the ultrasound transducer array 110 on the surface 150 to avoid accidental movement of at least some of the elongate support members 110 relative to other elongate support members during use of the ultrasound transducer array 110 as previously explained.

Following displacement, the plurality of sensors 115 are used to generate sensor data indicative of the respective relative displacements of the elongate support members 110 caused by the positioning of the ultrasound transducer array 100 on the surface 150. This sensor data may be received in 205 by the control unit of the ultrasound system 10 and processed in 207 to determine the relative displacements of the elongate support members 110. The control unit may optionally check in 209 if at least some of these relative displacements exceed a defined displacement threshold, which as previously explained may lead to interference (reverberation) artefacts. If this is the case, the method 200 may proceed to 211 in which the ultrasound transducer tiles 120 having an acoustic aperture 140 suffering from such interference due to a relatively large displacement of a neighboring elongate support member 110 may be excluded from the ultrasound beam forming as explained in more detail above. Otherwise, the method 200 may proceed to 213 in which the control unit may operate the ultrasound transducer array 100, e.g. steer the respective ultrasound transducer tiles 120 in the array, in accordance with the determined relative displacements of the elongate support members 110 before terminating in 215.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound transducer array comprising:
a plurality of elongate support members displaceable and/or deformable relative to each other in an elongation direction of the plurality of elongate support members, to establish conformal contact between end surfaces of the plurality of elongate support members and a surface of a subject;
a plurality of ultrasound transducer tiles mounted to the end surfaces of the plurality of elongate support transducer tile members, respectively; and
a plurality of sensors mounted to the plurality of elongate support members, respectively, wherein each sensor of the plurality of sensors is configured to detect relative displacement and/or deformation of the elongate support member to which the sensor is mounted in relation to an adjacent elongate support member of the plurality of elongate support members.

2. The ultrasound transducer array of claim 1, wherein each elongate support member comprises at least one sensor of the plurality of sensors.

3. The ultrasound transducer array of claim 1, wherein each sensor is an optical sensor facing a surface along the elongation direction of the adjacent elongate support member, the surface of the adjacent elongate support member carrying an optical pattern, wherein the optical sensor is configured to detect the relative displacement and/or deformation of the adjacent elongate support member based on detection of the optical pattern by the optical sensor.

4. The ultrasound transducer array of claim 3, wherein the optical pattern comprises a location-unique coding pattern.

5. The ultrasound transducer array of claim 1, further comprising:
a locking mechanism for locking the plurality of elongate support members in the relative displacement and/or deformation.

6. The ultrasound transducer array of claim 5, wherein the locking mechanism comprises an adjustable strap or clamp surrounding the plurality of elongate support members.

7. The ultrasound transducer array of claim 1, wherein each elongate support member of the plurality of elongate support members has a polygonal cross-section normal to the elongation direction.

8. The ultrasound transducer array of claim 1, wherein at least one elongate support member of the plurality of elongate support members is removable.

9. The ultrasound transducer array of claim 1, wherein the end surfaces of the plurality of elongate support members define a contoured surface.

10. The ultrasound transducer array of claim 9, wherein each end surface comprises a conformable coupling layer configured to achieve desired conformal coupling between the ultrasound transducer array 100 and the surface.

11. The ultrasound transducer array of claim 1, wherein each ultrasound transducer tile plurality of ultrasound transducer tiles comprises an array of ultrasound transducer elements.

12. An ultrasound system, comprising:
an ultrasound transducer array, comprising:
a plurality of elongate support members displaceable and/or deformable relative to each other in an elongation direction of the plurality of elongate support members to establish conformal contact between end surfaces of the plurality of elongate support members and a surface of a subject;
a plurality of ultrasound transducer tiles mounted to the end surfaces of the plurality of elongate support members, respectively; and
a plurality of sensors mounted to the plurality of elongate support members. respectively, wherein each sensor of the plurality of sensors is configured to detect relative displacement and/or deformation of the elongate support member to which the sensor is mounted in relation to an adjacent elongate support member of the plurality of elongate support members; and
a control unit configured to operate the plurality of ultrasound transducer tiles in response to sensor data provided by the plurality of sensors.

13. A method of operating an ultrasound system comprising an ultrasound transducer array that includes a plurality of elongate support members displaceable and/or deformable relative to each other in an elongation direction of the plurality of elongate support members, a plurality of ultrasound transducer tiles mounted to end surfaces of the plurality of elongate support members, respectively; and a plurality of sensors mounted to the plurality of elongate support members, respectively, the method comprising:
positioning the ultrasound transducer array on a surface of a subject;
receiving sensor data from the plurality of sensors indicative of respective relative displacements and/or deformations of the plurality of elongate support members caused by the positioning in relation to adjacent elongate support members of the plurality of elongate support members, respectively; and
determining the respective relative displacements and/or deformations of the elongate support members from the received sensor data.

14. The method of claim 13, further comprising:
locking the plurality of elongate support members upon positioning the ultrasound transducer array on the surface of the subject to maintain the respective relative displacements and/or deformations of the elongate support members.

15. The method of claim 13, further comprising:
excluding from ultrasound beam forming an ultrasound transducer tile suffering from interference due an elongate support member to which the ultrasound transducer tile is mounted having a displacement relative to an adjacent elongate support member exceeding a defined threshold.

16. The ultrasound system of claim 12, wherein the ultrasound system is an ultrasonic diagnostic imaging system.

17. The ultrasound transducer array of claim 1, wherein the plurality of sensors are mounted on elongate side surfaces of the plurality of elongate support members, respectively, facing elongate side surfaces of the adjacent an elongate support members, wherein the side surfaces are perpendicular to the respective end surfaces.

18. The ultrasound transducer array of claim 1, further comprising:

guide members and guide channels, configured to receive the guide members, extending along respective elongate side surfaces of the plurality of elongate support members, wherein the guide members and the guide channels are configured to provide friction sufficient to retain the relative displacement and/or deformation of the elongate support members in relation to the respective adjacent elongate support members up to a predetermined force in the elongate direction.

19. The ultrasound transducer array of claim 1, further comprising:

a mounting frame comprising a plurality of apertures configured to receive the plurality of elongate support members, respectively, wherein the plurality of apertures provide friction sufficient to retain the relative displacement and/or deformation of the elongate support members in relation to the respective adjacent elongate support members up to a predetermined force in the elongate direction.

20. The ultrasound system of claim 12, wherein each sensor of the ultrasound transducer array comprises optical sensor facing a surface along the elongation direction of the adjacent elongate support member, the surface of the adjacent elongate support member carrying an optical pattern, wherein the optical sensor is configured to detect the relative displacement and/or deformation of the adjacent elongate support member based on detection of the optical pattern by the optical sensor.

\* \* \* \* \*